United States Patent
Dong et al.

(10) Patent No.: US 10,800,733 B2
(45) Date of Patent: Oct. 13, 2020

(54) ACETOPHENONE COMPOUND, PREPARATION METHOD THEREFOR, AND APPLICATION THEREOF IN BLOOD LIPID REGULATION

(71) Applicant: Shanghai Bioenergy Medicine Science & Technology Co., Ltd., Shanghai (CN)

(72) Inventors: Yuqiong Dong, Shanghai (CN); Quanhai Liu, Shanghai (CN); Yu Shen, Shanghai (CN); Wentao Cai, Shanghai (CN)

(73) Assignee: Shanghai Bioenergy Medicine Science & Technology Co., Ltd., Shanghai (CN)

( * ) Notice: Subject to any disclaimer, the term of this patent is extended or adjusted under 35 U.S.C. 154(b) by 0 days.

(21) Appl. No.: 16/346,516

(22) PCT Filed: Mar. 15, 2018

(86) PCT No.: PCT/CN2018/079180
§ 371 (c)(1),
(2) Date: Apr. 30, 2019

(87) PCT Pub. No.: WO2018/166504
PCT Pub. Date: Sep. 20, 2018

(65) Prior Publication Data
US 2019/0292137 A1    Sep. 26, 2019

(30) Foreign Application Priority Data

Mar. 17, 2017    (CN) .......................... 2017 1 0160403
Mar. 17, 2017    (CN) .......................... 2017 1 0161146

(51) Int. Cl.
| | | |
|---|---|---|
| *C07C 235/24* | (2006.01) | |
| *A61P 3/06* | (2006.01) | |
| *C07C 231/02* | (2006.01) | |
| *C07D 213/807* | (2006.01) | |
| *C07D 213/82* | (2006.01) | |
| *A61K 31/455* | (2006.01) | |
| *A61K 31/16* | (2006.01) | |
| *C07D 213/803* | (2006.01) | |
| *A61K 31/167* | (2006.01) | |
| *C07C 235/16* | (2006.01) | |
| *C07D 213/80* | (2006.01) | |
| *A61K 31/44* | (2006.01) | |

(52) U.S. Cl.
CPC ............ *C07C 235/24* (2013.01); *A61K 31/16* (2013.01); *A61K 31/167* (2013.01); *A61K 31/455* (2013.01); *A61P 3/06* (2018.01); *C07C 231/02* (2013.01); *C07C 235/16* (2013.01); *C07D 213/80* (2013.01); *C07D 213/803* (2013.01); *C07D 213/807* (2013.01); *C07D 213/82* (2013.01)

(58) Field of Classification Search
None
See application file for complete search history.

(56) References Cited

FOREIGN PATENT DOCUMENTS

| | | | |
|---|---|---|---|
| CN | 102838505 A | 12/2012 | |
| CN | 103044250 A | 4/2013 | |
| EP | 3225618 A1 * | 10/2017 | ........... A61K 31/517 |
| WO | WO-2010002075 A1 * | 1/2010 | ........... C07D 405/04 |
| WO | WO-2016084816 A1 * | 6/2016 | ........... C07D 413/14 |

OTHER PUBLICATIONS

Sheikh et al, CA 151: 528574 (Abstract of Indian Journal of Heterocyclic Chemistry, 18(4) pp. 333-336) (Year: 2009).*
Sheikh et al, Indian Journal of Heterocyclic Chemistry, 18(4) pp. 333-336 (Year: 2009).*
WIPO, State Intellectual Property Office of the P.R. China International Search Authority, International Search Report and Written Opinion dated Jun. 27, 2018 in International Patent Application No. PCT/CN2018/079180, 9 pages.
Dehmel, F. et al., "Trithiocalbonates as a Novel Class of HDAC Inhibitors: SAR Studies, Isoenzyme Selectivity, and Pharmacological Profiles," *J. Med. Chem*, 51(13), Jun. 18, 2008, 17 pages.

* cited by examiner

*Primary Examiner* — Zinna Northington Davis
(74) *Attorney, Agent, or Firm* — Inskeep IP Group, Inc.

(57) ABSTRACT

Disclosed are a compound represented by Formula I or a pharmaceutically acceptable salt thereof, a preparation method therefor, the Formula I, and an application thereof in preparing drugs for regulating blood lipids.

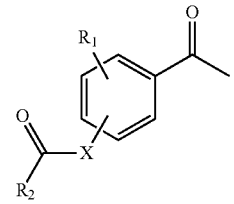

8 Claims, No Drawings

ACETOPHENONE COMPOUND, PREPARATION METHOD THEREFOR, AND APPLICATION THEREOF IN BLOOD LIPID REGULATION

RELATED APPLICATIONS

This application is the United States National Stage entry under 35 U.S.C. 371 of PCT/CN2018/079180 entitled Acetophenone Compound, Preparation Method Therefor, And Application Thereof In Blood Lipid Regulation, filed on Mar. 15, 2018, which in turn claims the priorities of Chinese patent application No. 201710161146.8 entitled Acetophenone Compound, Preparation Method Thereof, And Application Thereof In Fatty Liver Prevention And Treatment filed on Mar. 17, 2017, and Chinese patent application No. 201710160403.6 entitled Acetophenone Compound, Preparation Method Therefor, And Application Thereof In Blood Lipid Regulation filed on Mar. 17, 2017, all of which are hereby incorporated by reference in their entireties.

FIELD OF THE INVENTION

The invention belongs to the field of design and synthesis of new medicaments, and particularly relates to new amino-acetophenone-based compounds, preparation method thereof, and use thereof in regulating blood lipids.

BACKGROUND OF THE INVENTION

Abnormal lipid metabolism or transportation can lead to level(s) of one or more kind(s) of lipid(s) in plasma higher than normal, which is known as hyperlipidemia. Hyperlipidemia is a systemic disease characterized by excessive-high level of total cholesterol (TC) and/or triglyceride (TG) or excessive-low level of high density lipoprotein cholesterol (HDL-C) in blood, which is known as dyslipidemia by modern medicine. Since lipids are insoluble or slightly soluble in water and have to be present in the form of lipoproteins by combination with proteins, hyperlipidemia is also generally referred to as hyperlipoproteinemia.

Now, there are more than 160 million patients with hyperlipidemia in China. Hyperlipidemia is seriously harmful, and its damage to a body is dormant, gradual, progressive and systemic. Hyperlipidemia often accelerates systemic atherosclerosis, while vital organs of a body rely on blood and oxygen supplies from arteries. Once the arteries are blocked by atherosclerotic plaques, there will be serious consequences. For example, renal failure and other diseases caused by arteriosclerosis are all closely related to hyperlipidemia. A lot of researches have shown that hyperlipidemia is an independent and important risk factor for stroke, coronary heart disease, myocardial infarction and sudden cardiac death. In China, 2.6 million people die of cardiovascular diseases every year, wherein the cardiovascular diseases kill one person every 12 seconds on average, and more than 2 million patients for the first time get stroke attack every year in which two-thirds of them would die or become disabled. Many patients with hyperlipidemia may unconsciously get myocardial infarction, stroke and sudden death. Therefore, hyperlipidemia is also called a "silent killer" for human health.

In addition, hyperlipidemia is also an important risk factor for accelerating hypertension, abnormal glucose tolerance and diabetes. Hyperlipidemia may further lead to fatty liver, cirrhosis, cholelithiasis, pancreatitis, fundus bleeding, blindness, peripheral vascular diseases, claudication, hyperuricemia. Some patients with primary and familial hyperlipidemia may also have tendon, or nodular palm surface and periorbital xanthoma, Arcusjuvenilis or the like.

In view of the harm of hyperlipidemia to human bodies, especially the threat of cardiovascular diseases directly associated with it, blood lipid-regulating medicaments have always been an important field for new drug development. A large number of clinical studies have shown that some lipid-lowering drugs can reduce the incidence of atherosclerosis and coronary heart disease, the fatality rate of coronary heart disease and the incidence of myocardial infarction. Moreover, lipid contents in atherosclerotic plaques can be reduced, and fibers can be reinforced to stabilize the plaques through the treatment of lipid-lowering drugs, thereby reducing the incidence of severe diseases such as myocardial infarction and cerebral infarction caused by plaque rupture. Further, the blood lipid-regulating medicaments can restore the function of impaired vascular endothelial cells, prevent thrombosis, delay the progression of human atherosclerosis, decrease and eliminate formed plaques. Therefore, active application of the blood lipid-regulating medicaments is an important means to alleviate atherosclerosis and reduce the incidence of coronary heart disease.

At present, there are many drugs for clinical regulation of blood lipids, which include four major categories: cholic acid chelating agents (e.g., cholestyramine, colestipol), 3-hydroxyl-3-methylglutaryl coenzyme A (HMG-CoA) reductase inhibitors (e.g., lovastatin, pravastatin, atorvastatin and other statins), niacin and its derivatives (e.g., niacin, acipimox), phenoxy-aryl acids (e.g., clofibrate, ciprofibrate, fenofibrate, gemfibrozil). Other drugs or health care products having lipid-lowering effects comprise probucol, pantethine, elastase, $\omega$-3 fatty acids and the like.

In recent years, these blood lipid-regulating medicaments have played a significant role in lowering the levels of blood cholesterol and low-density lipoprotein (LDL-C), thus prevent and reduce the incidence of serious clinical events such as atherosclerosis and coronary heart disease. However, the existing blood lipid-regulating medicaments have certain side effects. For example, the statins, which is most widely used currently, may cause digestive system conditions such as upper abdominal discomfort after long-term use, and meantime, a considerable number of patients may have liver function damage, transaminase elevation, muscle pain, creatine kinase elevation and other adverse effects. Therefore, it is desired to design new chemical structures and develop new lipid-lowering pharmaceuticals with better therapeutic effect and less side effect.

SUMMARY OF THE INVENTION

An object of the invention is to provide novel aminoacetophenone-based compounds which have the function of in vivo regulation of blood lipids. It is demonstrated by experiments that such compounds can reduce cholesterol and low-density lipoprotein in blood of high-lipid model animals, and have good effect in reducing blood lipids.

In particular, the first aspect of the invention provides a compound of Formula I or a pharmaceutically acceptable salt thereof, Formula I

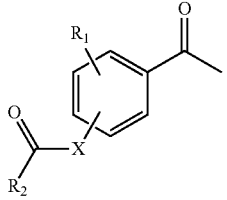

X is selected from oxygen or —NH;

$R_1$ is selected from H or hydroxyl;

$R_2$ is selected from the substituted groups of: phenyl; 5 to 6 membered monocyclic heteroaryl having 1 to 2 heteroatom(s) independently selected from nitrogen and oxygen; or

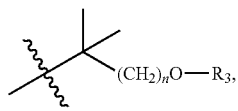

$R_3$ is independently selected from monosubstituted phenyl or disubstituted phenyl, wherein the substituent for phenyl is selected from halogen, hydroxyl, C1-C6 alkyl, C1-C6 alkoxy, C3-C6 cycloalkyl, C1-C6 alkyl substituted with C5-C10 aryl, C5-C10 aryl, 3 to 7 membered heterocyclyl having 1 to 3 heteroatom(s) independently selected from nitrogen, oxygen or sulfur, 5 to 7 membered heteroaryl cyclic group having 1 to 4 heteroatom(s) independently selected from nitrogen, oxygen or sulfur, substituted C1-C6 alkyl, substituted C3-C6 cycloalkyl, or substituted formyl, n is an integer selected from 0 to 5.

According to a preferred embodiment of the invention, the compound of Formula I or a pharmaceutically acceptable salt thereof may be provided wherein:

$R_2$ is selected from the substituted groups of: phenyl; 6 membered monocyclic heteroaryl having 1 to 2 heteroatom(s) independently selected from nitrogen; or

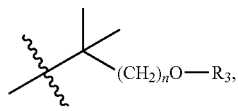

$R_3$ is independently selected from monosubstituted phenyl or disubstituted phenyl, wherein the substituent for phenyl is selected from halogen, hydroxyl, C1-C6 alkyl, C1-C6 alkoxy, C3-C6 cycloalkyl, C1-C6 alkyl substituted with C5-C10 aryl, C5-C10 aryl, 3 to 7 membered heterocyclyl having 1 to 3 heteroatom(s) independently selected from nitrogen, oxygen or sulfur, 5 to 7 membered heteroaryl cyclic group having 1 to 4 heteroatom(s) independently selected from nitrogen, oxygen or sulfur, substituted C1-C6 alkyl, substituted C3-C6 cycloalkyl, or substituted formyl, n is an integer selected from 0 to 5.

According to a more preferred embodiment of the invention, the compound of Formula I or a pharmaceutically acceptable salt thereof may be provided wherein:

$R_2$ is selected from the substituted groups of: phenyl; 6 membered monocyclic heteroaryl having 1 to 2 heteroatom(s) independently selected from nitrogen; or

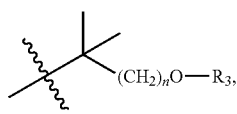

$R_3$ is independently selected from a monosubstituted phenyl or disubstituted phenyl, wherein the substituent for phenyl is selected from halogen, hydroxyl, C1-C3 alkyl, C1-C3 alkoxy, C3-C6 cycloalkyl, substituted C1-C3 alkyl, substituted C3-C6 cycloalkyl, n is an integer selected from 0 to 5.

According to a more preferred embodiment of the invention, the compound of Formula I or a pharmaceutically acceptable salt thereof may be provided wherein:

$R_2$ is selected from the substituted groups of: phenyl; 6 membered monocyclic heteroaryl having 1 to 2 heteroatom(s) independently selected from nitrogen; or

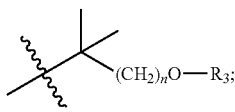

$R_3$ is independently selected from a monosubstituted phenyl or disubstituted phenyl, wherein the substituent for phenyl is selected from halogen, C1-C3 alkyl, n is an integer selected from 0 to 3.

According to a particularly preferred embodiment of the invention, $R_2$ is pyridin-3-yl.

According to a particularly preferred embodiment of the invention, $R_3$ is 2,5-dimethylphenyl.

According to a particularly preferred embodiment of the invention, n is 3.

According to a particularly preferred embodiment of the invention, the compound of Formula I of the invention may be any of the following compounds:

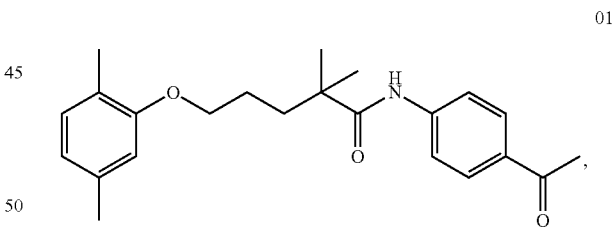

01

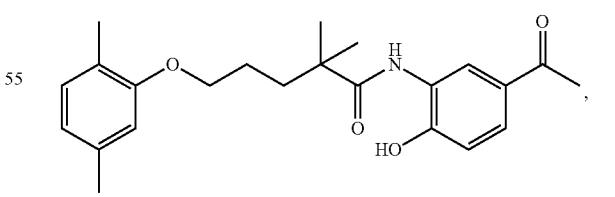

02

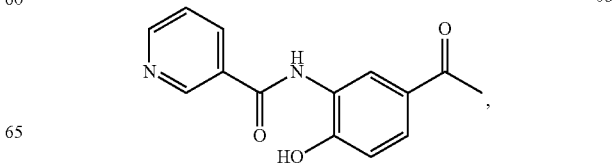

03

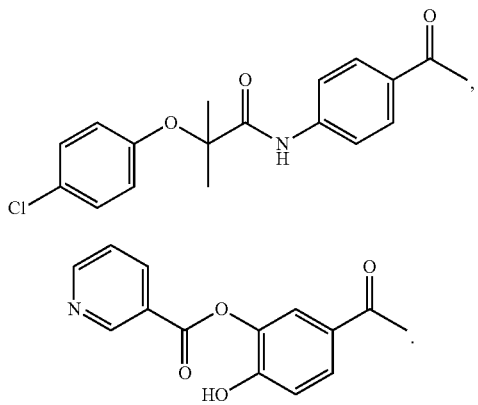

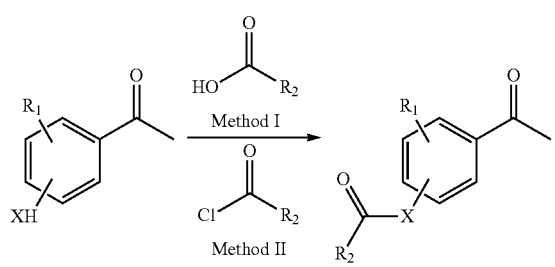

Unless otherwise stated, the following terms in this specification and claims of the invention have the following meanings.

The term "heteroaryl" as used herein indicates a stable monocyclic or bicyclic group having up to 6 atoms in each ring, wherein at least one of the rings is an aromatic ring and has 1 to 4 heteroatom(s) selected from O, N, and S. Within the scope of this definition, heteroaryl includes, but are not limited to, acridinyl, carbazolyl, cinnolinyl, quinoxalinyl, pyrazolyl, indolyl, benzotriazolyl, furyl, thienyl, benzothienyl, benzofuranyl, quinolyl, isoquinolyl, oxazolyl, isoxazolyl, indolyl, pyrazinyl, pyridazinyl, pyridyl, pyrimidinyl, pyrrolyl, tetrahydroquinolyl. "Heteroaryl" should be further understood to include any N-oxide derivative of nitrogen-containing heteroaryl. If the heteroaryl substituent is a bicyclic substituent in which one ring is a non-aromatic ring or does not contain any heteroatom, it should be understood that the linking is achieved by an aromatic ring or by a ring containing a heteroatom, respectively.

Unless otherwise defined, the substituent referred to by the term "substituted" as used herein may comprises: halogen, hydroxyl, C1-C6 alkyl, C1-C6 alkoxy, C1-C6 haloalkoxy, C1-C6 haloalkyl, C3-C6 cycloalkyl, C1-C6 alkyl substituted with C5-C10 aryl, C5-C10 aryl, 3 to 7 membered heterocyclyl having 1 to 3 heteroatom(s) independently selected from nitrogen, oxygen or sulfur, 5 to 7 membered heteroaryl ring group having 1 to 4 heteroatom(s) independently selected from nitrogen, oxygen or sulfur, C1-C6 ester or cyano group.

In the present invention, the pharmaceutically acceptable salt is preferably an acid addition salt obtained by a reaction of a compound of the invention with a pharmaceutically acceptable acid, or is a salt obtained by a reaction of a compound having an acidic group with a basic compound. Said acid is preferably selected from inorganic acids such as hydrochloric acid, sulfuric acid, phosphoric acid or hydrobromic acid, or from organic acids such as oxalic acid, maleic acid, fumaric acid, malic acid, tartaric acid, citric acid or benzoic acid. Said basic compound is preferably selected from sodium hydroxide, potassium hydroxide, calcium hydroxide, sodium carbonate, potassium bicarbonate or the like. The above pharmaceutically acceptable salt can be easily isolated, and can be purified by conventional isolation methods such as solvent extraction, dilution, recrystallization, column chromatography, and preparative thin layer chromatography.

The second aspect of the invention provides a method for preparing the above compound of Formula I or a pharmaceutically acceptable salt thereof.

In general, the compound of Formula I can be prepared according to the following process.

The above process provides two preparation methods of the compound of Formula I.

Method I comprises a step of directly condensing an acid

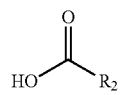

with a compound

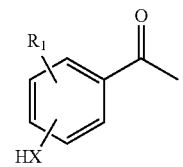

in the presence of a condensing agent and a solvent.

According to a preferred embodiment of the invention, the condensing agent is a commonly used amide-condensing agent such as 2-(7-azobenzotriazole)-N,N,N',N'-tetramethyluronium hexafluorophosphate, N,N'-carbonyldiimidazole, dicyclohexylcarbodiimide, diisopropylcarbodiimide, and the like.

According to a preferred embodiment of the invention, the solvent is selected from amide-based solvents such as N,N-dimethylformamide, N,N'-dimethylacetamide and N-methylpyrrolidone, halohydrocarbon such as dichloromethane, dichloroethane and chloroform, ester solvents such as ethyl acetate and isopropyl acetate, cyclic ether solvents such as tetrahydrofuran and dioxane.

According to a preferred embodiment of the invention, a nitrogen-containing catalyst such as N,N-dimethylaminopyridine may be added to accelerate the reaction.

Method II comprises a step of condensing an acyl chloride and a compound

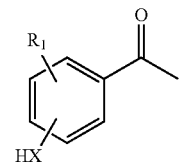

in a solvent, wherein the acyl chloride is obtained by a reaction of an acid

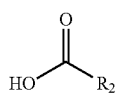

with a chlorinating agent.

According to a preferred embodiment of the present invention, the halogenating agent comprises oxalyl chloride, thionyl chloride, phosphorus trichloride, phosphorus pentachloride, thionyl bromide, phosphorus tribromide and the like.

According to a preferred embodiment of the invention, the solvent is selected from amide-based solvents such as N,N-dimethylformamide, N,N'-dimethylacetamide and N-methylpyrrolidone, halohydrocarbon such as dichloromethane, dichloroethane and chloroform, ester solvents such as ethyl acetate and isopropyl acetate, cyclic ether solvents such as tetrahydrofuran and dioxane.

According to a preferred embodiment of the invention, the condensation reaction can be accelerated by adding an inorganic base such as sodium hydroxide, potassium hydroxide, sodium carbonate and potassium carbonate, or an organic base such as triethylamine, pyridine and diisopropylethyl amine.

The third aspect of the invention provides a pharmaceutical composition comprising the compound of Formula I or a pharmaceutically acceptable salt thereof, as well as a pharmaceutically acceptable additive.

The compounds of the invention can be formulated into pharmaceutical compositions with various conventional additives such as diluents and excipients. Depending on the therapeutic purpose, the pharmaceutical compositions can be formulated into various types of unit dosage forms for administration, such as tablet, pill, powder, solution, suspension, emulsion, granule, capsule, suppository and injection (solution or suspension).

Any excipient known and widely used in the art can be used in order to form the pharmaceutical compositions into tablets. For example, the excipient can be a carrier such as lactose, white sugar, sodium chloride, glucose, urea, starch, calcium carbonate, kaolin, crystalline cellulose, and silicic acid; a binder such as water, ethanol, propanol, common syrup, dextrose solution, starch solution, gelatin solution, carboxymethyl cellulose, shellac, methyl cellulose, potassium phosphate, and polyvinylpyrrolidone; a disintegrating agent such as dry starch, sodium alginate, agar powder and kelp powder, sodium bicarbonate, calcium carbonate, polyethylene sorbitan fatty acid ester, sodium lauryl sulfate, monoglyceride stearate, starch and lactose; a disintegration inhibitor such as white sugar, glyceryl tristearate, coconut oil and hydrogenated oil; an adsorption enhancer such as quaternary ammonium bases and sodium lauryl sulfate; a wetting agent such as glycerin and starch; an adsorbent such as starch, lactose, kaolin, bentonite and colloidal silicic acid; and a lubricant such as pure talc, stearate, boric acid powder and polyethylene glycol. If desired, the tablet might be sugar-coated tablet, gelatin film-coated tablet, enteric-coated tablet, film-coated tablet, two-layer film-coated tablet, or multilayer-coated tablet, by using conventional coating materials.

Any excipient known and widely used in the art may be used in order to form the pharmaceutical composition into pills. For example, the excipient can be a carrier such as lactose, starch, coconut oil, hardened vegetable oil, kaolin and talc; a binder such as acacia gum powder, tragacanth gum powder, gelatin and ethanol; a disintegrating agent such as agar and kelp powder.

Any excipient known and widely used in the art may be used in order to form the pharmaceutical composition into suppository. For example, the excipient can be polyethylene glycol, coconut oil, higher alcohols, esters of higher alcohols, gelatin, semi-synthetic glycerides, and the like.

In order to prepare a pharmaceutical composition in an injection form, the solution or suspension may be sterilized, and is preferably added with an appropriate amount of sodium chloride, glucose, glycerin or the like so as to prepare an injection which is isotonic with blood. Any carrier commonly used in the art can be used for preparing the injection. For example, the carrier may be water, ethanol, propylene glycol, ethoxylated isostearyl alcohol, polyoxylated isostearyl alcohol, polyethylene sorbitan fatty acid ester and the like. In addition, conventional solubilizers, buffers, analgesics, and the like can be added. Further, coloring agents, preservatives, flavors, flavoring agents, aromatizers, or other pharmaceuticals may be added as needed, during the treatment of schizophrenia.

The content of the compound shown by Formula I of the invention or a pharmaceutically acceptable salt thereof in the pharmaceutical composition is not specially limited, and can be selected within a wide range. It generally can be 1-70% by weight, preferably be 1-30% by weight.

The administration route of the pharmaceutical composition in the invention is not specially limited. And various dosage forms can be selected for administration depending on the age, sex and other conditions and symptoms of the patient. For example, the pharmaceutical composition in a tablet, pill, solution, suspension, emulsion, granule or capsule form can be administered orally; the pharmaceutical composition in an injection form can be administered alone or intravenously in combination with injectable solution such as glucose solution or amino acid solution, and if necessary, the injection can be used alone for intramuscular, intradermal, subcutaneous or intraperitoneal injection; and the pharmaceutical composition in a suppository form can be administered into rectum.

In the invention, the administration dose can be appropriately selected depending on the administration method, the age, sex, and other conditions and symptoms of the patient. A typical administration dose may be about 0.1 to 300 mg pharmaceutically active ingredient/kg body weight/day. Generally, each unit dosage form can comprise 1 to 200 mg of the pharmaceutically active ingredient.

The fourth aspect of the invention provides use of the compound of Formula I or a pharmaceutically acceptable salt thereof in the manufacture of a medicament for regulating blood lipids.

The invention comprises the following beneficial effects. The compound of the invention not only can lower the triglyceride level in the blood of high fat model animals, but also has good effect in lowering cholesterol and low density lipoprotein. The compounds of the invention have relatively low toxicity with acute toxicity of $ID_{50} \geq 5$ g/kg.

DETAILED DESCRIPTION OF THE EMBODIMENTS

EXAMPLE 1

Preparation of Compound 01

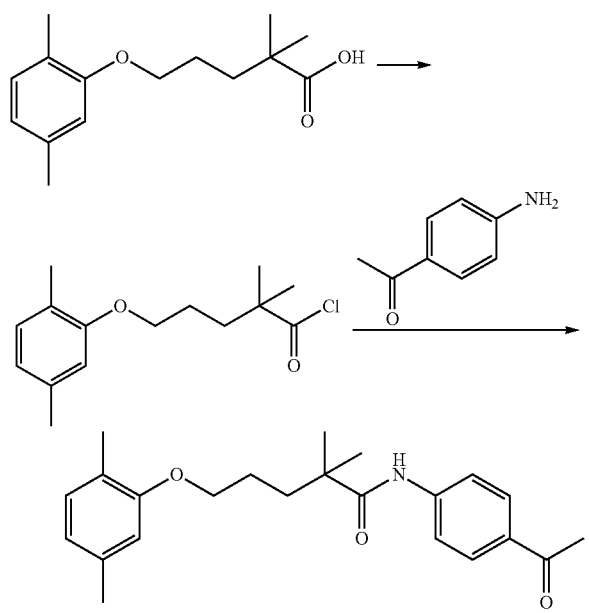

4.0 g of 5-(2,5-dimethylphenoxy)-2,2-dimethylpentanoic acid was dissolved in 40 mL of dichloromethane, and 3.0 g of oxalyl chloride and 2 drops of N,N-dimethylformamide were added under cooling in an ice bath. Then, the ice bath was removed and the mixture was warmed to room temperature and stirred for 3 hours. The solvent was evaporated to dryness to give corresponding acyl chloride.

2.2 g of p-aminoacetophenone was dissolved in 30 mL of pyridine, and the above acyl chloride in 20 mL of dichloromethane solution was added dropwise under cooling in an ice bath. After addition, the ice bath was removed, and the mixture was warmed to room temperature and stirred for 1 hour. The solvent was evaporated to dryness, and the residue was dissolved by adding 200 mL of ethyl acetate, and washed successively with 100 mL of 3N hydrochloric acid, 100 mL of water and 100 mL of saturated brine. Then, the solvent was evaporated to dryness to give 5.4 g of the target product by silica-gel column chromatography. $^1$H NMR (400 MHz, CDCl$_3$) δ 7.95-7.89 (m, 2H), 7.62 (d, J=8.8 Hz, 2H), 7.56 (s, 1H), 6.99 (d, J=7.5 Hz, 1H), 6.66 (d, J=7.5 Hz, 1H), 6.59 (s, 1H), 3.97-3.88 (m, 2H), 2.57 (s, 3H), 2.28 (s, 3H), 2.14 (s, 3H), 1.82 (dd, J=15.4, 2.8 Hz, 4H), 1.35 (s, 6H). MS (ESI) m/z: 390.2 [M+23]$^+$.

EXAMPLE 02

Preparation of Compound 02

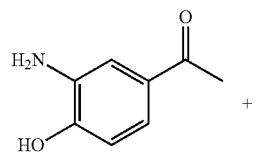

+

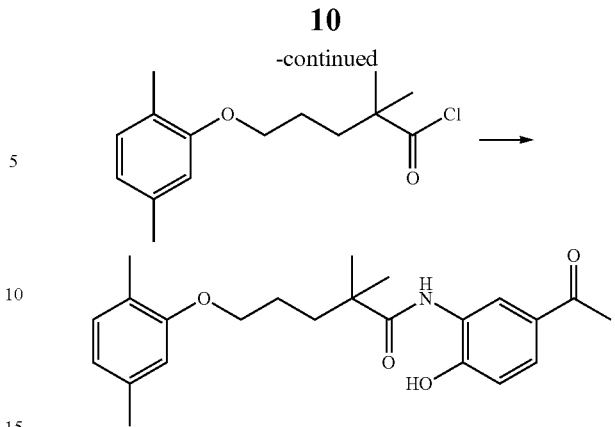

3.5 g of 1-(3-amino-4-hydroxylphenyl)ethanone was dissolved in 100 mL of pyridine. 9.3 g of 5-(2,5-dimethylphenoxy)-2,2-dimethyl valeryl chloride in 20 mL of dichloromethane was added dropwise under cooling in an ice bath, after which the ice bath was removed and the mixture was warmed to room temperature and stirred for 2 hours. The solvent was evaporated to dryness, and the residue was dissolved by adding 200 mL of ethyl acetate, and washed successively with 100 mL of 3N hydrochloric acid, 60 mL of water and 30 mL of saturated brine. The solvent was evaporated to dryness. With ethyl acetate as the solvent, 5.1 g of the target compound was obtained through recrystallization. $^1$H NMR (400 MHz, CDCl$_3$) δ 9.99 (s, 1H), 7.82 (s, 1H), 7.71 (dt, J=6.2, 2.0 Hz, 2H), 7.04 (d, J=8.3 Hz, 1H), 6.99 (d, J=7.4 Hz, 1H), 6.65 (d, J=7.5 Hz, 1H), 6.60 (s, 1H), 3.95 (t, J=5.4 Hz, 2H), 2.53 (s, 3H), 2.29 (s, 3H), 2.16 (s, 3H), 1.91-1.78 (m, 4H), 1.40 (s, 6H). MS (ESI) m/z: 406.2 [M+23]$^+$.

EXAMPLE 03

Preparation of Compound 03

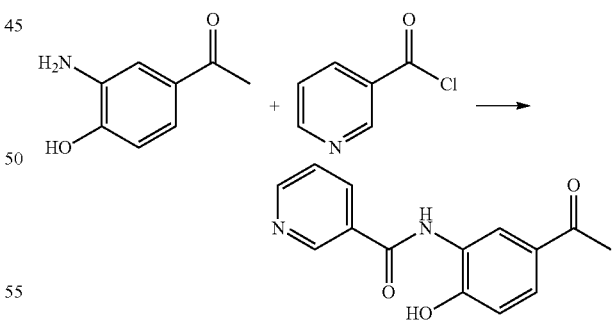

2.7 g of 1-(3-amino-4-hydroxylphenyl)ethanone was dissolved in 50 mL of pyridine, and 6.4 g of nicotinyl chloride was added under cooling in ice bath. Then, the ice bath was removed and the mixture was warmed to room temperature and stirred for 2 hours. The solvent was evaporated to dryness. 50 mL of water and 50 mL of saturated sodium carbonate aqueous solution was added. Extraction with 300 mL of dichloromethane was conducted. The organic phase was washed with 100 mL of saturated brine, and the solvent

11 was evaporated to dryness. The residue was dissolved in 100 mL of methanol, and added with 30 mL of 4N sodium hydroxide aqueous solution. The mixture was stirred at room temperature for 1 hour, and was adjusted to pH 8-9 by adding hydrochloric acid. The solid was collected by filtration. 3.0 g of the target product was obtained by silica-gel column chromatography. $^1$H NMR (400 MHz, DMSO-$d_6$) δ 10.82 (s, 1H), 9.24 (d, J=1.5 Hz, 1H), 8.89 (dd, J=4.8, 1.6 Hz, 1H), 8.45 (dt, J=8.0, 1.9 Hz, 1H), 7.85-7.74 (m, 2H), 7.67-7.59 (m, 1H), 7.07 (d, J=8.4 Hz, 1H), 2.49 (s, 3H). MS (ESI) m/z: 257.1 [M+1]$^+$.

EXAMPLE 4

Preparation of Compound 04

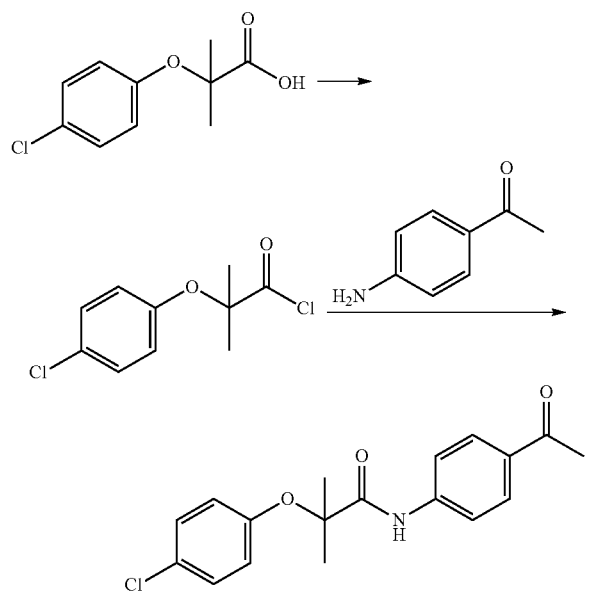

7.1 g of 2-(4-chlorophenoxy)-2-methylpropanoic acid was dissolved in 100 mL of dichloromethane, and 6.3 g of oxalyl chloride and 2 drops of N,N-dimethylformamide was added under cooling in ice bath. Then, the ice bath was removed and the mixture was warmed to room temperature and stirred for 3 hours. The solvent was evaporated to dryness to give corresponding acyl chloride.

4.05 g of p-aminoacetophenone was dissolved in 50 mL of pyridine. The above acyl chloride in 50 mL of dichloromethane solution was added dropwise under cooling in ice bath, after which the ice bath was removed and the mixture was warmed to room temperature and stirred for 2 hours. Then, the solvent was evaporated to dryness, and the residue was added with 300 mL of water. The solid was collected by filtration, and then was homogenized with 50 ml of mixed solvents of petroleum ether:ethyl acetate in 5:1. The solid was collected by filtration and dried to give 8.5 g of the target compound. $^1$H NMR (400 MHz, CDCl$_3$) δ 8.72 (s, 1H), 7.96 (d, J=8.6 Hz, 2H), 7.69 (d, J=8.6 Hz, 2H), 7.27 (d, J=9.1 Hz, 2H), 6.93 (d, J=8.7 Hz, 2H), 2.58 (s, 3H), 1.57 (s, 6H). MS (ESI) m/z: 332.3 [M+1]$^+$.

EXAMPLE 05

Preparation of Compound 05

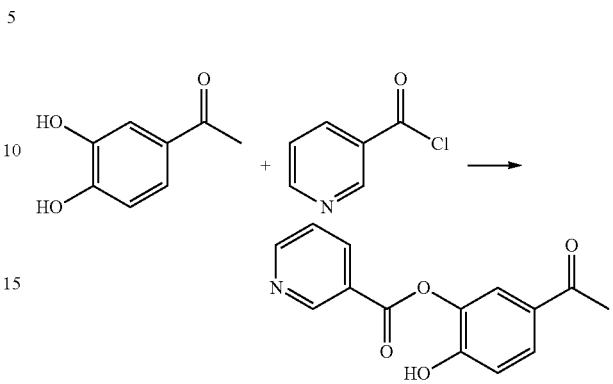

0.46 g of 1-(3,4-dihydroxylphenyl)ethanone and 0.40 g of triethylamine were dissolved in 25 mL of dichloromethane, and 0.54 g of nicotinyl chloride was added under cooling in an ice bath. Then, the ice bath was removed and the mixture was warmed to room temperature and stirred for 1 hour. The reaction mixture was diluted with 50 mL of dichloromethane, washed successively with 20 mL of water and 20 mL of saturated brine. Then the solvent was evaporated to dryness. The residue was added with 10 mL of saturated sodium carbonate aqueous solution and stirred. The resulted mixture was extracted twice with 30 mL of ethyl acetate. The aqueous phase was separated and adjusted to pH 7-8 by adding 1N hydrochloric acid, and then extracted three times with 30 mL of a mixture of dichloromethane and methanol (dichloromethane:methanol=10:1). The organic phases were combined and washed with 30 mL of saturated brine. The solvent was evaporated to dryness to give 0.14 g of the target product. $^1$H NMR (400 MHz, DMSO-$d_6$) δ 10.81 (s, 1H), 9.24 (d, J=1.6 Hz, 1H), 8.89 (dd, J=4.8, 1.6 Hz, 1H), 8.45 (dt, J=8.0, 1.9 Hz, 1H), 7.86-7.75 (m, 2H), 7.64 (dd, J=7.9, 4.9 Hz, 1H), 7.05 (t, J=9.9 Hz, 1H), 2.48 (s, 3H). MS (ESI) m/z: 258.2 [M+1]$^+$.

Pharmacological and Biological Activity Tests

1. Therapeutic Effect on Hyperlipidemia of SD Rats

Preparation process of lipid emulsion: 500 g of lard oil was taken, placed in a container, and heated to melt. When the temperature rose to 100° C., 200 g of cholesterol was added. After complete dissolution, 20 g of propylthiouracil was further added. The resulted mixture was stirred well, and added with 500 ml of Tween 80 after dissolution, resulting in an oil phase. At the same time, 600 mL of distilled water and 400 mL of 1,2-propanediol were taken and heated to 60° C. in a water bath, and then was added with 40 g of sodium deoxycholate. The resulted mixture was stirred well until complete dissolution was achieved, so as to give an aqueous phase. The aqueous phase was added into the oil phase and mixed well to give a lipid emulsion.

Process for modeling: Animals were fed adaptively for 3 days. Then, according to the body weight, 5 animals were selected as control and the remaining animals were intragastrically administered with the lipid emulsion during 9:00 to 11:00 am every day with 1 mL/100 g body weight for 2 weeks. After fasted for 12 hours, 1 mL of blood was collected from the orbits of the animals, and was determined by Hitachi Automatic Biochemical Analyzer 7080 for serum cholesterol (CHO), triglyceride (TG), low density lipoprotein (LDL-C) and high density lipoprotein (HDL-C). The animals having 4-7 mmol/L of CHO were used in the experiments.

According to the body weight, the animals, which were administrated with the lipid emulsion for 2 weeks, were divided into Model group, Simvastatin group (Sim, 10 mg/kg), Compound 01 group (80 mg/kg), Compound 02 group (80 mg/kg), Compound 03 group (80 mg/kg), Compound 04 group (80 mg/kg), Compound 05 group (80 mg/kg), Compound A group (80 mg/kg), with 5 animals in each group. The animals were continued with the intragastric administration of the lipid emulsion, and at the same time, the pharmaceutical-administered groups were administrated with the corresponding doses of pharmaceuticals, while the Model group was administrated with an equal volume of the solvent. The animals were administrated with the lipid emulsion in the morning and pharmaceuticals in the afternoon. The animals were measured for the body weight every Monday, and were observed. After 21 days of continuous administration, the animals were fasted for 12 hours. Then, 1 mL of blood was collected from the orbits, and was determined by Hitachi Automated Biochemical Analyzer 7080 for serum cholesterol (CHO), triglyceride (TG), low density lipoprotein (LDL-C) and high density lipoprotein (HDL-C).

The controls used in this experiment comprised Compound A and Simvastatin (also referred to as Sim herein).

Compound A is disclosed by a Chinese patent with application no. 201110174070.5, and has the following formula.

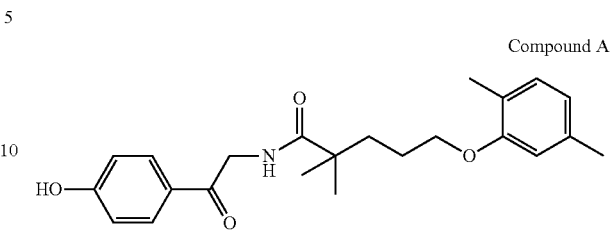

The experimental results were shown by Table 1. The formula for calculating the blood lipid-reducing effect is: (CHO of Model group —CHO of pharmaceutical-administrated group)/CHO of Model group*100%. According to this formula, the blood lipid-reducing effect of each compound was obtained and shown in Table 1 with reference to the reduction ratio of cholesterol and the level of triglyceride of each group, wherein the reduction ratio of cholesterol of each group of compound is as follows: Compound 01: (10.66−4.29)/10.66*100%=59.75%; Compound 02: (10.66−4.86)/10.66*100%=54.40%; Compound 03: (10.66−4.56)/10.66*100%=57.22%; Compound 04: (10.66−4.90)/10.66*100%=54.03%; Compound 05: (10.664.63)/10.66*100%=56.56%; Compound A: (10.66−6.15)/10.66*100%=42.30%. In this experiment, the effects of the compounds obtained herein for regulating blood lipids can be determined by using the blood cholesterol reduction as the main indicator, with reference to the decrease of triglyceride.

TABLE 1

| | \multicolumn{4}{c}{the level of blood lipids in rats administrated with samples ($\bar{X} \pm SD$)} | | | |
|---|---|---|---|---|
| | TG (mmol/L) | CHO (mmol/L) | HDL-C (mmol/L) | LDL-C (mmol/L) |
| Compound 01 (80 mg/kg) | 0.47 ± 0.27** | 4.29 ± 0.65** | 2.02 ± 0.27 | 3.07 ± 1.25** |
| Compound 02 (80 mg/kg) | 0.51 ± 0.19** | 4.86 ± 1.08** | 1.94 ± 0.49 | 3.18 ± 0.71** |
| Compound 03 (80 mg/kg) | 0.71 ± 0.16 | 4.56 ± 1.24** | 1.81 ± 0.27 | 3.14 ± 1.06** |
| Compound 04 (80 mg/kg) | 0.50 ± 0.15** | 4.90 ± 1.09** | 2.00 ± 0.52 | 3.27 ± 1.34** |
| Compound 05 (80 mg/kg) | 0.56 ± 0.23** | 4.63 ± 0.41** | 1.95 ± 0.50 | 3.12 ± 0.34** |
| Compound A (80 mg/kg) | 0.58 ± 0.11** | 6.15 ± 2.12* | 1.41 ± 0.28 | 4.97 ± 1.07** |
| Sim (10 mg/kg) | 0.60 ± 0.07* | 6.28 ± 0.76* | 1.65 ± 0.26 | 4.54 ± 0.36** |
| Model | 0.81 ± 0.23 | 10.66 ± 2.55## | 1.87 ± 0.51# | 8.37 ± 2.16## |
| Control | 0.59 ± 0.15 | 1.36 ± 0.21 | 1.20 ± 0.20 | 0.35 ± 0.04 |

Note:
pharmaceutical-adminstered groups compared with Model group,

*P < 0.05,

**P < 0.01;

p < 0.05, p < 0.01 vs Control

As shown by Table 1, all of Compounds 01, 02, 03, 04 and 05 have relatively good blood lipid-reducing effects, and can significantly reduce the level of cholesterol.

2. Acute Toxicity Test

Single oral dose method was used.

Animal: ICR mice, body weight of 18-20 g, 20 mice in each group, half male and half female. Experimental pharmaceuticals: Compound 01 (5 g/kg), Compound 02 (5 g/kg), Compound 03 (5 g/kg), Compound 04 (5 g/kg), Compound 05 (5 g/kg). The pharmaceuticals were added with 0.5% CMC-Na, ground and mixed well, stored until use.

Experimental process: After fasted for 16 h, the animals were orally and intragastrically administered with tested pharmaceuticals in a single dose respectively. After administration, the mice were fasted for another 3-4 h. The general conditions of the animals were closely observed for 6 h after the administration, and further observed for 14 days.

Experimental results: No animal died during the experiment and no abnormal condition was observed.

Acute toxicity: ID50 ≥ 5 g/kg.

What is claimed is:

1. A compound of Formula I or a pharmaceutically acceptable salt thereof,

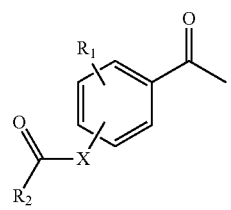

Formula I wherein,

X is oxygen;

$R_1$ is selected from hydroxyl;

$R_2$ is selected from the substituted pyridyl, wherein the substituent for pyridyl is halogen; hydroxyl; C1-C6 alkyl; C1-C6 alkoxy; C1-C6 haloalkoxy; C1-C6 haloalkyl; C3-C6 cycloalkyl.

2. The compound of Formula I or a pharmaceutically acceptable salt thereof according to claim 1, wherein $R_2$ is pyridin-3-yl.

3. A compound or a pharmaceutically acceptable salt thereof, comprising the following structural formula:

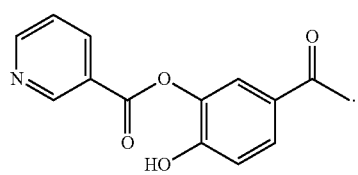

05

4. A method of preparing the compound of Formula I or a pharmaceutically acceptable salt thereof

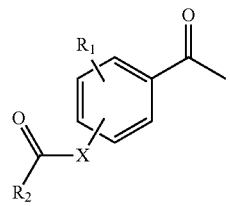

Formula I wherein,

X is oxygen;

$R_1$ is selected from hydroxyl;

$R_2$ is selected from the substituted pyridyl, wherein the substituent for pyridyl is halogen; hydroxyl; C1-C6 alkyl; C1-C6 alkoxy; C1-C6 haloalkoxy; C1-C6 haloalkyl; C3-C6 cycloalkyl, the method comprising:

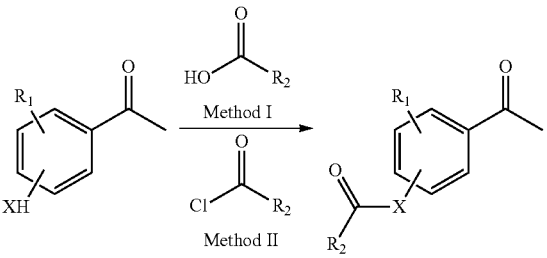

Method I, comprising a step of directly condensing an acid

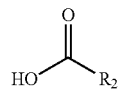

and a compound

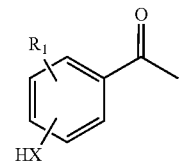

in the presence of a condensing agent and a solvent; or

Method II, comprising a step of condensing an acyl chloride and a compound

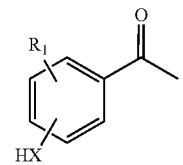

in a solvent, wherein the acyl chloride is obtained by a reaction of an acid

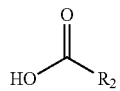

with a chlorinating agent.

5. A pharmaceutical composition comprising the compound of Formula I or a pharmaceutically acceptable salt thereof as defined in claim 1, as well as a pharmaceutically acceptable additive.

6. The pharmaceutical composition according to claim 5, wherein the pharmaceutical composition is in a form of tablet, pill, powder, liquid, suspension, emulsion, granule, capsule, suppository or injection.

7. A method for regulating blood lipids comprising administrating a therapeutically effective amount of the compound of Formula I or a pharmaceutically acceptable salt thereof as defined in claim 1 to a subject in need thereof.

8. A method for regulating blood lipids comprising administrating a therapeutically effective amount of the pharmaceutical composition as defined in claim 5 to a subject in need thereof.

* * * * *